(12) United States Patent
Stinson

(10) Patent No.: US 7,784,936 B2
(45) Date of Patent: Aug. 31, 2010

(54) OPHTHALMIC SOLUTION DISPENSING DEVICE

(76) Inventor: Steve Stinson, 23436 W. Magnolia St., Buckeye, AZ (US) 85326

( * ) Notice: Subject to any disclaimer, the term of this patent is extended or adjusted under 35 U.S.C. 154(b) by 218 days.

(21) Appl. No.: 12/070,447

(22) Filed: Feb. 19, 2008

(65) Prior Publication Data
US 2009/0207373 A1 Aug. 20, 2009

(51) Int. Cl.
*G02C 1/00* (2006.01)
*A61U 35/00* (2006.01)

(52) U.S. Cl. ........................ 351/158; 604/300

(58) Field of Classification Search ................ 351/158, 351/41; 604/295–302; 128/898
See application file for complete search history.

(56) References Cited

U.S. PATENT DOCUMENTS

| | | | |
|---|---|---|---|
| 676,379 A | 6/1901 | Young | |
| 852,827 A | 5/1907 | Dorment | |
| 1,006,945 A | 10/1911 | Houston | |
| 1,991,345 A | 2/1935 | Durand | |
| 2,883,983 A | 4/1959 | Bierdman | |
| 4,468,103 A * | 8/1984 | Meckler | 351/158 |
| 4,908,024 A | 3/1990 | Py | |
| 5,171,306 A | 12/1992 | Vo | |
| 5,255,024 A | 10/1993 | Jensen | |
| 5,368,582 A | 11/1994 | Bertera | |
| 5,569,224 A | 10/1996 | Michalos | |
| 5,836,927 A * | 11/1998 | Fried | 604/300 |
| 5,989,217 A | 11/1999 | Ohki et al. | |
| 6,736,802 B1 | 5/2004 | Recanati | |
| 2003/0032930 A1 | 2/2003 | Brunch | |

* cited by examiner

*Primary Examiner*—Hung X Dang
(74) *Attorney, Agent, or Firm*—The Halvorson Law Firm

(57) ABSTRACT

A device for dispensing ophthalmic solutions to a user's eyes comprising a container for holding ophthalmic solutions, transfer tubing attached to the container for dispensing and applying said solution and a clip attached to the container for attaching said applicator to eyeglasses. The transfer tubing is the clip by being formed into the shape of a clip for attaching said eye solution applicator to eyeglasses.

16 Claims, 3 Drawing Sheets

OPHTHALMIC SOLUTION DISPENSING DEVICE

FIELD OF THE INVENTION

The present invention relates to the field of ophthalmic solution dispensing devices. More specifically, the present invention relates to ophthalmic solution dispensing devices that are mountable onto glasses for easy solution dispensing.

BACKGROUND

Tears bathe the eye, washing out dust and debris and keeping the eye moist. They also contain enzymes that neutralize the microorganisms that colonize the eye. Tears are essential for good eye health.

In dry eye syndrome, the eye doesn't produce enough tears, or the tears have a chemical composition that causes them to evaporate too quickly.

Dry eye syndrome has several causes. It occurs as a part of the natural aging process, especially during menopause, as a side effect of many medications, such as antihistamines, antidepressants, certain blood pressure medicines, Parkinson's medications, and birth control pills; or dry, dusty or windy climates. Home or office air conditioning or a dry heating system can also dry out eyes. Another cause is insufficient blinking, such as when a person stares at a computer screen all day.

Dry eyes are also a symptom of systemic diseases such as lupus, rheumatoid arthritis, rosacea or Sjogren's syndrome (a triad of dry eyes, dry mouth, and rheumatoid arthritis or lupus).

Long-term contact lens wear is another cause; in fact, dry eyes are the most common complaint among contact lens wearers. Recent research indicates that contact lens wear and dry eyes can be a vicious cycle. Dry eye syndrome makes contact lenses feel uncomfortable, and the rubbing of the lenses against the conjunctiva seems to be a cause of dry eyes.

Incomplete closure of the eyelids, eyelid disease and a deficiency of the tear-producing glands are other causes. Tears are composed of three layers: the outer, oily, lipid layer; the middle, watery, lacrimal layer; and the inner, mucous or mucin layer. Each layer is produced by a different part of the eye (the lacrimal gland produces the lacrimal layer, for example), so a problem with any of those sources can result in dry eyes.

Dry eye syndrome is more common in women, possibly due to hormone fluctuations. Recent research suggests that smoking, too, can increase the risk of dry eye syndrome. With increased popularity of eyelid surgery for improved appearance, dry eye complaints now occasionally are associated with incomplete closure of eyelids following a procedure.

Dry eye syndrome is an ongoing condition that may not be cured (depends on the cause), but the accompanying dryness, scratchiness and burning can be managed. Artificial tears can be used, which are lubricating eyedrops that may alleviate the dry, scratching feeling.

Restasis eyedrops (cyclosporine in a castor oil base) go one step further: they help the eyes to increase tear production.

Sometimes people use the eye drops that "get the red out" to treat their dry eyes. This won't work unless the eye drops also contain artificial tears, and the original "get-the-red-out" formulation doesn't. These drops can reduce or eliminate the redness temporarily, but they don't treat the cause of the redness, whether it's dryness, environmental irritation, or some other problem.

Not only that, but the vasoconstrictors in those formulas that reduce redness by contracting the eye's blood vessels are addictive, in the sense that over time, more and more is needed to achieve the same effect. And with frequent use, the effect diminishes after a while, anyway—the blood vessels simply won't constrict as much as they did when you first used the drops.

Thus there is a clear and present need for new and improved devices and methods for the treatment of dry eye syndrome.

SUMMARY OF THE INVENTION

It is an object of the present invention to provide a device for dispensing ophthalmic solutions to a user's eyes.

It is another object of the present invention to provide A clip on eye solution applicator comprising a container for holding ophthalmic solutions, transfer tubing attached to the container for dispensing and applying said solution and a clip attached to the container for attaching said applicator to eyeglasses.

It is yet another object of the present invention to provide a clip on eye solution applicator wherein the transfer tubing is the clip by being formed into the shape of a clip for attaching said eye solution applicator to eyeglasses.

It is still yet a further object of the present invention to provide a clip on eye solution applicator wherein said tubing has one transfer hole and said container has one transfer hole aligned with said tubing transfer hole whereby solution is capable of transfer between the container and tubing, said tubing and container one hole configuration impairing the ability to refill the clip on eye solution applicator.

It is a further object of the present invention to provide a clip on eye solution applicator wherein said tubing has two transfer holes with a blockage between them and said container has two transfer holes aligned with said tubing transfer holes whereby solution is capable of transfer between the container and tubing, said tubing and container two hole configuration aiding the ability to refill the clip on eye solution applicator.

The novel features that are considered characteristic of the invention are set forth with particularity in the appended claims. The invention itself, however, both as to its structure and its operation together with the additional object and advantages thereof will best be understood from the following description of the preferred embodiment of the present invention when read in conjunction with the accompanying drawings. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the Description of Preferred Embodiments is not intended to indicate a desire to invoke the special provision of 35 U.S.C. §112, paragraph 6 to define the invention. To the contrary, if the provisions of 35 U.S.C. §112, paragraph 6, are sought to be invoked to define the invention (s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. §112, paragraph 6. Moreover, even if the provisions of 35 U.S.C. §112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

BRIEF DESCRIPTION OF THE ILLUSTRATED EMBODIMENTS

DESCRIPTION of the ILLUSTRATED EMBODIMENT

Figure 1:
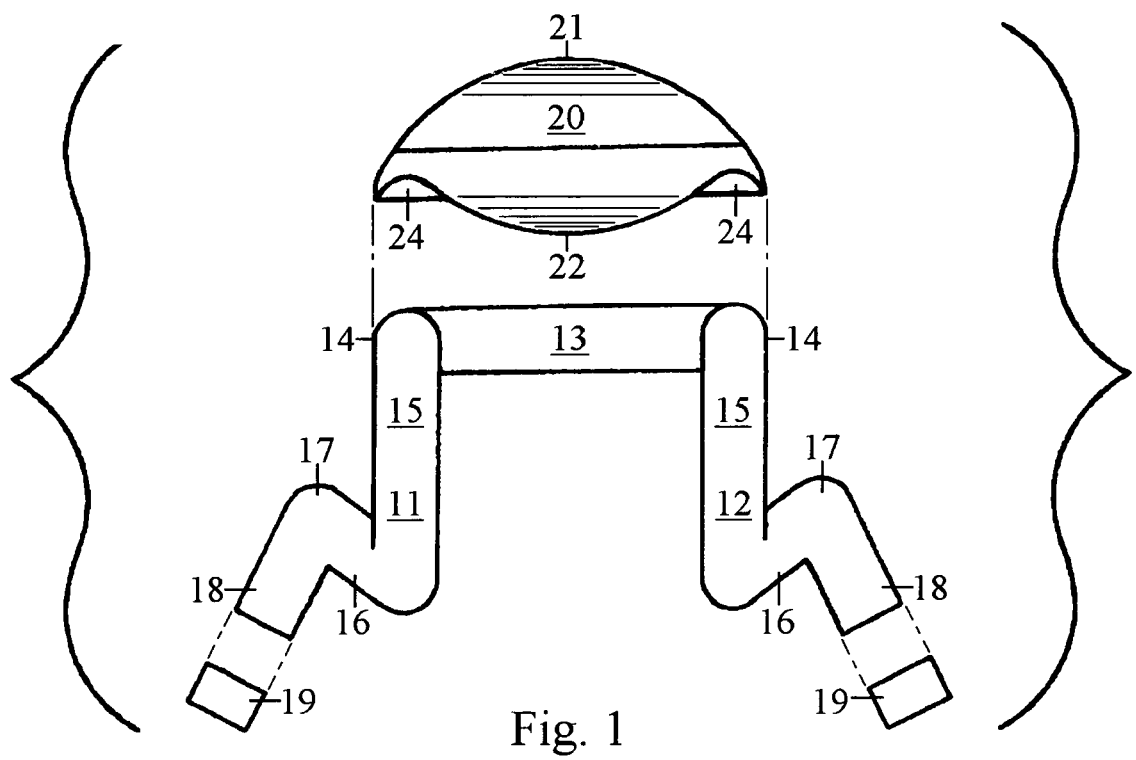
FIG. 1 is an exploded top view showing the transfer tubing, solution container and nozzle caps of the clip on eye solution applicator.

With reference now to the drawing of the preferred invention.

Figure 2:
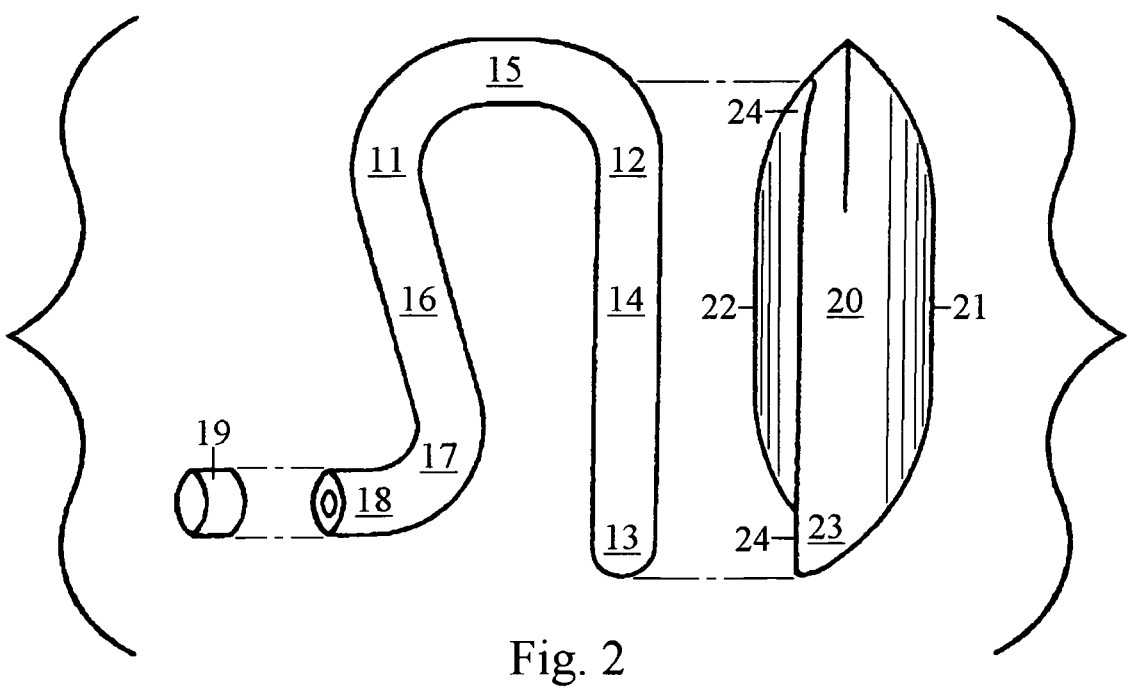
FIG. 2 is an exploded right side view showing the transfer tubing, solution container and nozzle caps of the clip on eye solution applicator.

FIG. 1 (in brackets) is an exploded top view and FIG. 2 (in brackets) is an exploded right side view wherein both views are of a new clip on ophthalmic solution applicator 10.

With reference to FIG. 1 and FIG. 2, an ophthalmic solution container 20 holds and dispenses the ophthalmic solution. The solution container 20 is preferably made from sterile grade plastic. It can be manufactured with a transfer tubing 12 attached as one piece or the solution container 20 may be made separately and attached onto the transfer tubing 12 when the applicator 10 is assembled during manufacturing.

The transfer tubing 12 transfers the ophthalmic solution from the solution container 20, through the nozzles 18 and ultimately to the users eyes. The transfer tubing 12 is preferably made from sterile grade plastic.

Nozzle caps 19 are tamper indicating and removable. They seal the nozzles 18 and preserve sterility. At least one nozzle cap 19 is removed before use. The nozzle caps 19 preferably are marked and sealed to the nozzles 18 in a way that when a nozzle cap 19 is removed there will be an indication that the nozzle 18 to nozzle cap 19 seal has been broken. The nozzle caps 19 can be formed as part of the nozzles 18 when the transfer tubing 12 and clip 11 are manufactured or the nozzle caps 19 can be made separately and attached onto the nozzles 18 after the transfer tubing 12 and clip 11 are manufactured.

Figure 3:
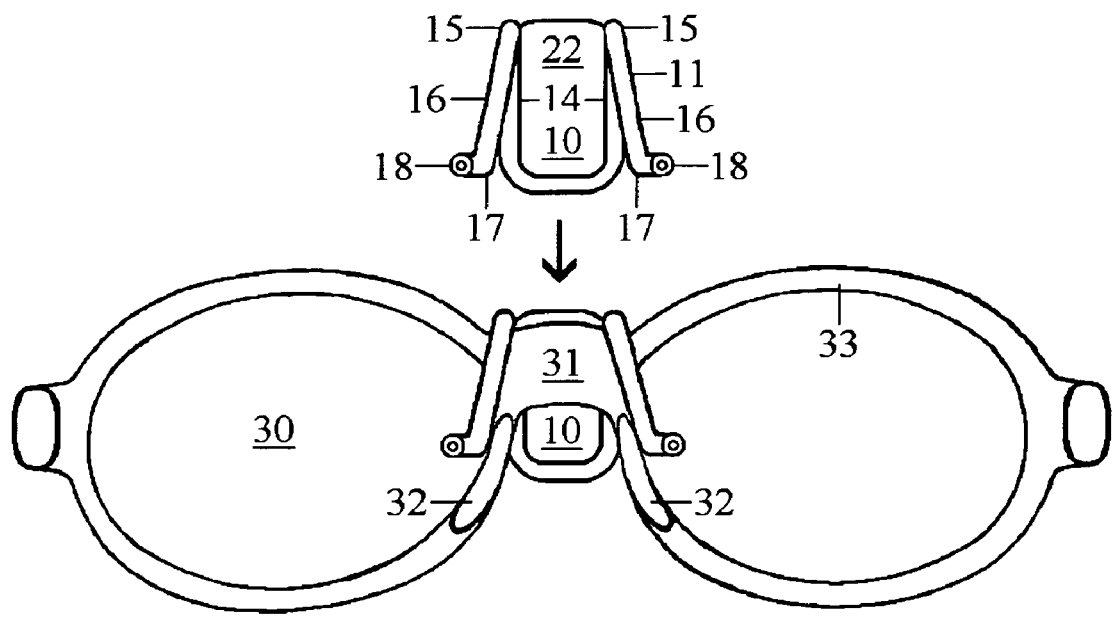
FIG. 3 is a view from behind a pair of common eyeglasses. This view shows the size perspective of the clip on eye solution applicator, how the applicator is clipped onto eyeglasses and how it would look from behind the eyeglasses.
Figure 4:
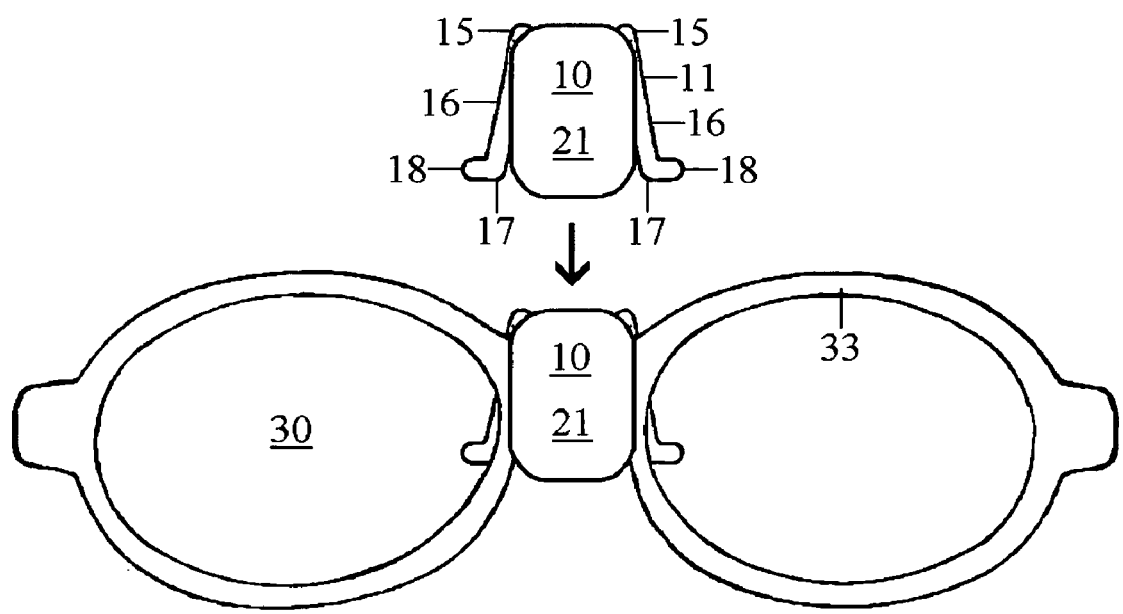
FIG. 4 is a view from in front of a pair of common eyeglasses. This view shows the size perspective of the clip on eye solution applicator, how the applicator is clipped onto eyeglasses and how it would look from in front of the eyeglasses.

FIG. 3 is a view from behind a pair of common eyeglasses 30 and FIG. 4 is a view from in front of a pair of common eyeglasses 30. This figure illustrates the size of the clip on eye solution applicator 10 as compared to eyeglasses 30.

With reference to FIG. 3 and FIG. 4, the transfer tubing 12 is formed into the shape of a clip 11, the parts of the clip 11 are doubled so there are two of each part. The doubled parts perform the same function together and are referenced in this description as a single clip 11 with single parts unless otherwise shown.

The clip 11 has four sections. When the clip on ophthalmic solution applicator 10 is attached to eyeglasses 30 an outside clip 14 pushes against the outside of the eyeglasses 30 at a bridge 31 and the eyeglass frame 33 adjacent to the bridge 31, this stabilizes and holds the clip on eye solution applicator 10 in position. A clip stop 15, stops the top of the clip 11 at the top of the eyeglass bridge 31, this stabilizes and positions the clip on eye solution applicator 10. An inside clip 16 acts as a spring for clip elbows 17, this provides clamping tension between the outside clip 14 and the clip elbows 17. The clip elbows 17 are separated by and apply a light clamping pressure onto the nose pads 32 and they push against the inside of the eyeglasses frame 33 at a point below the bridge 31, this positions the nozzles 18, stabilizes the clip on ophthalmic solution applicator 10 and holds the clip on eye solution applicator 10 in position on the eyeglasses 30.

The clip on opthalmic solution applicator 10 is attached to eyeglasses 30 by sliding the clip 11 over the eyeglass bridge 31 with the clip elbows 17 and inside clip 16 over the inside of the eyeglass bridge 31 and the solution container 20 and outside clip 14 over the outside of the eyeglasses bridge 31. The clip on eye solution applicator 10 is slid down over the eyeglass bridge 31 until the clip elbows 17 are separated by the nose pads 32 and the clip stop 15 rests on the top of the eyeglasses bridge 31.

The nozzles 18 are formed into the ends of the transfer tubing 12. They direct the delivery of ophthalmic solution to the user's eyes, they maintain stability and accuracy by applying clip elbow 17 pressure onto the nose pads 32, this uses the nose pads 32 as a support base for the nozzles 18.

With reference to FIG. 1 through FIG. 4, a container front wall 21 is the part of the solution container 20 that faces forward away from the eyeglasses 30 and can be seen from in front of the eyeglasses 30. The container front wall 21 is resiliently pliable, this is the location on the clip on eye solution applicator 10 where the user pushes to dispense and apply eye solution the eye.

A container back wall 22 is the part of the solution container 20 that faces rearward towards the eyeglasses 30 and can be seen from behind the eyeglasses 30. The bottom edge and the side edges of the container back wall 22 are formed into the shape of a tubing groove 24, which is where the bottom tubing 13 and outside clip 14 fit onto the solution container 20.

Figure 5:
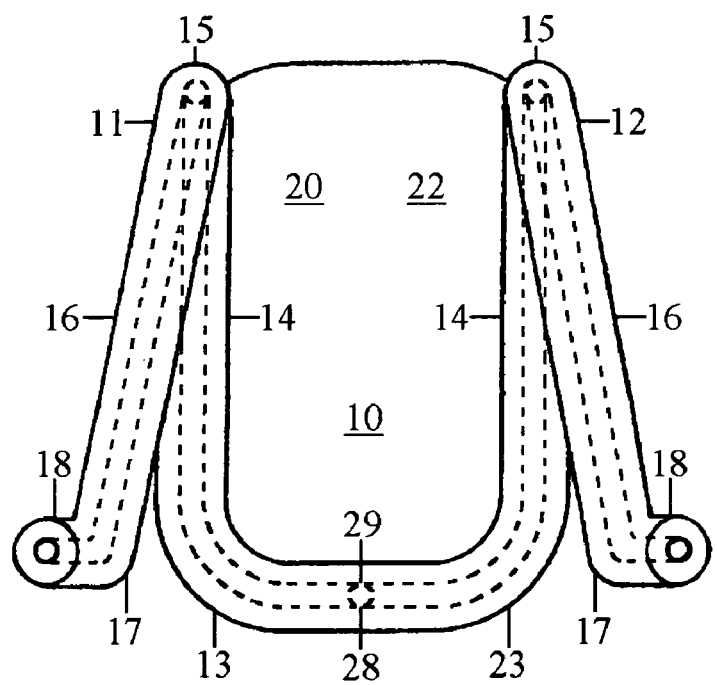
FIG. 5 is a back view showing the transfer tubing with the solution container behind it. This view shows the one hole configuration and fluid travel paths that make the clip on eye solution applicator difficult to refill.
Figure 6:
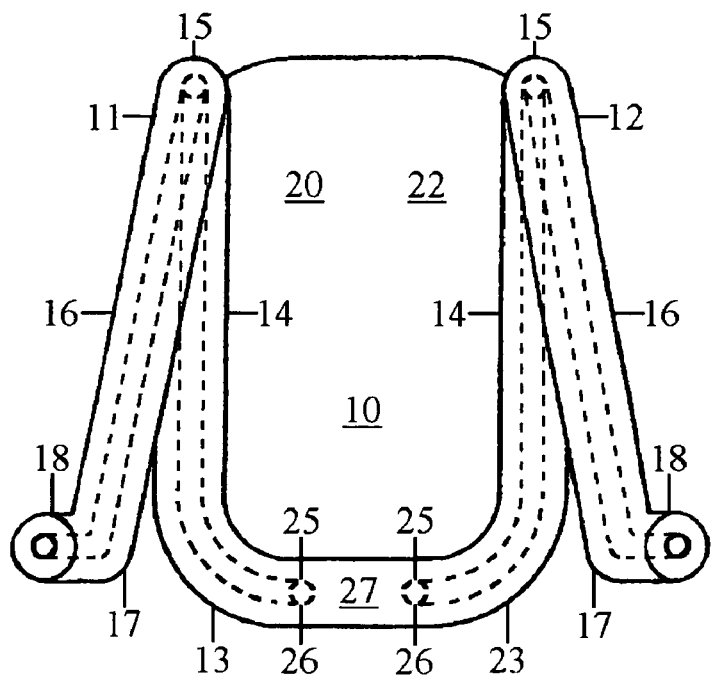
FIG. 6 is a back view showing the transfer tubing with the solution container behind it. This view shows the two hole configuration and fluid travel paths that make the clip on eye solution applicator easy to refill.

FIG. 5 and FIG. 6 are both back views of the new clip on ophthalmic solution applicator 10. The transfer tubing 12 with the solution container 20 behind it is shown in these views.

With reference to FIG. 5 and FIG. 6, a container bottom 23 is the location of the container single transfer hole 29 or the container double transfer hole 25. This is where the ophthalmic solution is transferred from the solution container 20 to the transfer tubing 12.

The bottom tubing 13 is the location of the tubing single transfer hole 28 or tubing double transfer hole 26 and the hole separator 27, this is where the eye solution transfers between the solution container 20 and transfer tubing 12.

With reference to FIG. 1 through FIG. 6, the solution dispensing function is now described.

With the clip on ophthalmic solution applicator 10 in the normal upright position, air in the solution container 20 stays at the top of the solution container 20 away from the container single transfer hole 29 or the container double transfer hole 25 and the ophthalmic solution stays at the container bottom 23 with the container single transfer hole 29 or the container double transfer hole 25.

When the user pushes inward on the outside surface of the container front wall 21 the volume inside the solution container 20 is reduced, this applies pressure to the ophthalmic solution inside. The ophthalmic solution is pushed out of the container 20 through the container single transfer hole 29 or the container double transfer hole 25, through the tubing single transfer hole 28 or the tubing double transfer hole 26 and into the bottom tubing 13. The ophthalmic solution then travels from the bottom tubing 13 through the transfer tubing 12 and through the nozzles 18. At least one nozzle cap is removed prior to use. The ophthalmic solution is propelled from the nozzles 18 and applied to the user's eye. The amount of solution dispensed and applied to the user's eye depends on the amount of pressure applied by the user to the container front wall 21. When pressure is removed from the container front wall 21 the resilient wall returns back to its normal shape and the solution container returns back to its normal volume as air is drawn back in to replace the solution that was dispensed out.

There are two container and tubing transfer hole configurations shown in FIG. 5 and FIG. 6 of the drawing.

Shown in FIG. 5 is the container single transfer hole 29 and tubing single transfer hole 28 configurations. With the clip on ophthalmic solution applicator 10 in any position, this configuration impairs the ability to add solution to or refill the solution container 20. When some or all of the eye solution is used it will be relatively difficult to add solution to the clip on eye solution applicator 10 in this configuration. This configuration has one transfer hole in the bottom of the transfer tubing 12 and the solution container 20 has one transfer hole aligned with the tubing transfer hole.

With the clip on ophthalmic solution applicator 10 in the upright or in any position solution can be pushed in through one of the nozzles 18, the solution travels the transfer tubing 12 to the tubing single transfer hole 28 and container single hole 29. The solution will start to enter the solution container 20 but can't because the solution is pushing against air trapped in the solution container 20. The trapped air has only one hole to exit the solution container 20 from and that hole is being blocked by the solution trying to enter. The solution and air push against each other and block each other. If the other nozzle 18 is blocked, the solution will not enter the solution container 20 and will stop. If the other nozzle 18 is not blocked, the solution will not enter the solution container 20 but will be pushed past the tubing single transfer hole 28, through the transfer tubing 12 and exit through the other nozzle 18.

It will possible to refill the solution container 20 in the single transfer hole configuration by completely submerging the clip on ophthalmic solution applicator 10 in solution and forcing the air out by pushing in on the container front wall 21. By removing pressure from the container front wall 21 the resilient wall returns to its normal shape and the solution container 20 returns back to its normal volume as solution is drawn back into the solution container 20. This is not a convenient method for refilling the solution container 20, it would be difficult to make portable.

Shown in FIG. 6 is the container double transfer hole 25 and tubing double transfer hole 26 configurations. With the clip on eye solution applicator 10 in the inverted position, this configuration aids the ability to add solution to or refill the solution container 20 when some or all of the eye solution is used. It will be difficult to add solution to the solution container 20 in the double transfer hole configuration with the clip on eye solution applicator 10 in the upright position. This configuration has two transfer holes in the bottom of the transfer tubing 12 with a hole separator 27 between them and the solution container 20 has two transfer holes aligned with the tubing 12 transfer holes.

With the clip on eye solution applicator 10 in the upright position air in the solution container 20 stays at the top of the solution container 20 away from the container double transfer hole 25 and the eye solution stays at the container bottom 23 with the container double transfer hole 25.

When solution is pushed in through one of the nozzles 18 it travels the transfer tubing 12 to the tubing double transfer hole 26 and the hole separator 27. The tubing double transfer hole 26 is two tubing transfer holes with a separator 27 between them. The solution's path through the transfer tubing 12 is blocked by the hole separator 27. The solution will start to enter the solution container 20 but can't because the air in the solution container 20 is trapped at the top by the solution that is blocking the double transfer hole 26 at the container bottom 23. If the other nozzle 18 is blocked, the solution will not enter the solution container 20 and will stop. If the other nozzle 18 is not blocked, the solution will enter the solution container 20 but no solution will be added because of the trapped air in the solution container 20, whatever amount of solution that is pushed in through one transfer hole, that same amount of solution is pushed out of the other transfer hole and exits through the other nozzle 18.

It will be possible to refill the solution container 20 in the double transfer hole configuration with the clip on eye solution applicator 10 in the inverted or up side down position. Air in the solution container 20 stays at the container bottom 23 with the container double transfer hole 25 and the eye solution stays at the top of the solution container 20 away from the container double transfer hole 25.

When solution is pushed in through one of the nozzles 18 it travels the transfer tubing 12 to the tubing double transfer hole 26 and the hole separator 27. If the other nozzle 18 is not blocked, the solution enters the solution container 20 through one transfer hole and moves to the top of the solution container 20, away from the other transfer hole. The air at the container bottom 23 stays near the other transfer hole, as solution enters the solution container 20 from one transfer hole the air is pushed out through the other transfer hole and exits through the other nozzle 18. The solution that is pushed in through one nozzle will replace all of the air in the solution container 20 and in the transfer tubing 12, then the solution will exit through the other nozzle 18. The solution exiting through the other nozzle 18 indicates that the solution container 20 in full. This is a convenient method for refilling the solution container 20, it would be easy to make portable.

The preferred embodiment of the invention is described above in the Drawings and Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

What is claimed is:

1. A clip on eye solution applicator comprising:
a container for holding ophthalmic solutions, transfer tubing attached to the container for dispensing and applying said solution and a clip attached to the container for attaching said applicator to eyeglasses; wherein the transfer tubing is the clip by being formed into the shape of a clip for attaching said eye solution applicator to eyeglasses.

2. The clip on eye solution applicator as described in claim 1 wherein said transfer tubing further comprises at least one nozzle to direct the delivery of eye solution to at least one eye of the user wherein said at least one nozzle includes corresponding tamper indicating removable caps to seal the at least one nozzle and preserve sterility.

3. The clip on eye solution applicator as described in claim 2 wherein said tubing has one transfer hole and said container has one transfer hole aligned with said tubing transfer hole whereby solution is capable of transfer between the container and tubing, said tubing and container one hole configuration impairing the ability to refill the clip on eye solution applicator.

4. The clip on eye solution applicator as described in claim 2 wherein said tubing has two transfer holes with a blockage between them and said container has two transfer holes aligned with said tubing transfer holes whereby solution is capable of transfer between the container and tubing, said tubing and container two hole configuration aiding the ability to refill the clip on eye solution applicator.

5. The clip on eye solution applicator as described in claim 1 wherein said tubing has one transfer hole and said container has one transfer hole aligned with said tubing transfer hole whereby solution is capable of transfer between the container and tubing, said tubing and container one hole configuration impairing the ability to refill the clip on eye solution applicator.

6. The clip on eye solution applicator as described in claim 1 wherein said tubing has one transfer hole and said container has one transfer hole aligned with said tubing transfer hole whereby solution is capable of transfer between the container and tubing, said tubing and container one hole configuration impairing the ability to refill the clip on eye solution applicator.

7. The clip on eye solution applicator as described in claim 1 wherein said tubing has two transfer holes with a blockage between them and said container has two transfer holes aligned with said tubing transfer holes whereby solution is capable of transfer between the container and tubing, said tubing and container two hole configuration aiding the ability to refill the clip on eye solution applicator.

8. The clip on eye solution applicator as described in claim 1 wherein said tubing has two transfer holes with a blockage between them and said container has two transfer holes aligned with said tubing transfer holes whereby solution is capable of transfer between the container and tubing, said tubing and container two hole configuration aiding the ability to refill the clip on eye solution applicator.

9. A combination of a pair of eyeglasses and a clip on eye solution applicator comprising:
a container for holding ophthalmic solutions, transfer tubing attached to the container for dispensing and applying said solution and a clip attached to the container for attaching said applicator to eyeglasses; and a pair of eyeglasses; wherein the transfer tubing is the clip by being formed into the shape of a clip for attaching said eye solution applicator to eyeglasses.

10. The combination as described in claim 9 wherein said transfer tubing further comprises at least one nozzle to direct the delivery of eye solution to at least one eye of the user wherein said at least one nozzle includes corresponding tamper indicating removable caps to seal the at least one nozzle and preserve sterility.

11. The combination as described in claim 10 wherein said tubing has one transfer hole and said container has one transfer hole aligned with said tubing transfer hole whereby solution is capable of transfer between the container and tubing, said tubing and container one hole configuration impairing the ability to refill the clip on eye solution applicator.

12. The combination as described in claim 10 wherein said tubing has two transfer holes with a blockage between them and said container has two transfer holes aligned with said tubing transfer holes whereby solution is capable of transfer between the container and tubing, said tubing and container two hole configuration aiding the ability to refill the clip on eye solution applicator.

13. The combination as described in claim 9 wherein said tubing has one transfer hole and said container has one transfer hole aligned with said tubing transfer hole whereby solution is capable of transfer between the container and tubing, said tubing and container one hole configuration impairing the ability to refill the clip on eye solution applicator.

14. The combination as described in claim 9 wherein said tubing has one transfer hole and said container has one transfer hole aligned with said tubing transfer hole whereby solution is capable of transfer between the container and tubing, said tubing and container one hole configuration impairing the ability to refill the clip on eye solution applicator.

15. The combination as described in claim 9 wherein said tubing has two transfer holes with a blockage between them and said container has two transfer holes aligned with said tubing transfer holes whereby solution is capable of transfer between the container and tubing, said tubing and container two hole configuration aiding the ability to refill the clip on eye solution applicator.

16. The combination as described in claim 9 wherein said tubing has two transfer holes with a blockage between them and said container has two transfer holes aligned with said tubing transfer holes whereby solution is capable of transfer between the container and tubing, said tubing and container two hole configuration aiding the ability to refill the clip on eye solution applicator.

* * * * *